US010307355B2

(12) United States Patent
Rosa et al.

(10) Patent No.: US 10,307,355 B2
(45) Date of Patent: Jun. 4, 2019

(54) N-ARALKYLCARBONYLDIAMINE COMPOUNDS AND PERSONAL CARE COMPOSITIONS COMPRISING THE SAME

(71) Applicant: Conopco, Inc., Englewood Cliffs, NJ (US)

(72) Inventors: Jose Guillermo Rosa, Cheshire, CT (US); Jianming Lee, Monroe, CT (US); Diana Marrero, Bristol, CT (US); Jean Elizabeth Adamus, Guilford, CT (US); Stella Villa-Mora, Oakland, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/568,632

(22) PCT Filed: Apr. 7, 2016

(86) PCT No.: PCT/EP2016/057580
§ 371 (c)(1),
(2) Date: Oct. 23, 2017

(87) PCT Pub. No.: WO2016/173818
PCT Pub. Date: Nov. 3, 2016

(65) Prior Publication Data
US 2018/0161260 A1 Jun. 14, 2018

(30) Foreign Application Priority Data
Apr. 28, 2015 (EP) ..................................... 15165365

(51) Int. Cl.
*A61K 8/42* (2006.01)
*A61Q 19/08* (2006.01)
*C07C 233/40* (2006.01)
*C07C 235/34* (2006.01)

(52) U.S. Cl.
CPC ................ *A61K 8/42* (2013.01); *A61Q 19/08* (2013.01); *C07C 233/40* (2013.01); *C07C 235/34* (2013.01); *C07C 2601/08* (2017.05); *C07C 2601/14* (2017.05); *C07C 2601/16* (2017.05)

(58) Field of Classification Search
CPC . C07C 233/40; C07C 233/34; C07C 2601/16; C07C 2601/14; C07C 2601/08; A61Q 19/08; A61K 8/42
See application file for complete search history.

(56) References Cited

U.S. PATENT DOCUMENTS

| | | | |
|---|---|---|---|
| 4,677,120 A | 6/1987 | Parish et al. | |
| 4,885,311 A | 12/1989 | Parish et al. | |
| 5,049,584 A | 9/1991 | Purcell et al. | |
| 5,124,356 A | 6/1992 | Purcell et al. | |
| RE34,075 E | 9/1992 | Purcell et al. | |
| 5,192,779 A * | 3/1993 | Shiokawa | C07C 233/40 514/346 |
| 6,022,896 A | 2/2000 | Weinkauf et al. | |
| 6,379,716 B2 | 4/2002 | Santhanam et al. | |
| 6,440,432 B1 | 8/2002 | Mukherjee et al. | |
| 8,039,012 B2 | 10/2011 | McClellan et al. | |
| 2007/0004750 A1 | 1/2007 | Lorsbach et al. | |
| 2007/0287733 A1 | 12/2007 | Snorrason | |
| 2008/0269190 A1 | 10/2008 | Husfeld et al. | |
| 2009/0069335 A1 | 3/2009 | Ji et al. | |
| 2011/0033397 A1 | 2/2011 | Corstjens et al. | |
| 2011/0294851 A1 | 12/2011 | Ji et al. | |

FOREIGN PATENT DOCUMENTS

| | | |
|---|---|---|
| EP | 0441226 | 8/1991 |
| EP | 0367040 | 4/1993 |
| EP | 2912653 | 8/2008 |
| EP | FR2912653 | 8/2008 |
| GB | 2284154 | 5/1995 |
| WO | WO9718203 | 5/1997 |
| WO | WO0110427 | 2/2001 |
| WO | WO0146166 | 6/2001 |
| WO | WO03037271 | 5/2003 |
| WO | WO2006056752 | 6/2006 |
| WO | WO2009035542 | 3/2009 |
| WO | WO09068876 | 6/2009 |
| WO | WO2009079392 | 6/2009 |
| WO | WO2009150408 | 12/2009 |
| WO | WO2014114496 | 7/2014 |
| WO | WO2014180640 | 11/2014 |

OTHER PUBLICATIONS

Levine et al, Journal of Pharmacology and Experimental Therapeutics, The Physiological Disposition of Oxyphenonium Bromide (Antrenyl) and Related Compounds, 1957, 121(1), pp. 63-70. (Year: 1957).*
Smith et al, The Journal of Organic Chemistry, Physiologically Active Compounds. III. Hydrochlorides of Amino Esters of Phenylcyclohexylglycolic Acids . . . , 1951, pp. 1301-1309. (Year: 1951).*
Kurzen et al, Hormone and Metabolic Research, Non-neuronal Cholinergic System of Human Skin, 2007; 39, pp. 125-135. (Year: 2007).*
Zaugg et al., Tertiary Carbinols of the Piperazine Series., Journal of the American Chemical Society, 1958, pp. 2773-2774.
2-cyclohexyl-2-hydroxy-N-methyl-2-[henyl-N-(2-piperidin-1-ylethyl)acetamide, PubChem Database, 2011, pp. 1-6; XP55284000.
Mitsuya et al., A Potent, Long-Acting, Orally Active (2R)-2-[1R)-3,3-Difluorocyclopentyl]-2-hydroxy-2-phenylacetamide: A Novel Muscarinic M3 Receptor Antagonist with High Selectivity for M3 over M2 Receptors, Journal of Medicinal Chemistry, 2000, pp. 5017-5029; XP002547105, vol. 43 No. 26, US.

(Continued)

*Primary Examiner* — Paul A Zucker
(74) *Attorney, Agent, or Firm* — Edward A. Squillante, Jr.

(57) ABSTRACT

The present invention provides novel N-aralkylcarbonyldiamine compounds having a structure as set forth in Structure I. The structures are not quaternized. When these novel unquaternized compounds are used in personal care compositions, particularly personal care skin compositions, they are more stable and provide unexpected cosmetic advantages (e.g., against wrinkles, aging skin, etc.) when delivered from the personal care skin compositions.

7 Claims, No Drawings

(56) References Cited

OTHER PUBLICATIONS

Ogino et al., Muscarinic M3 Receptor Antagonists with (2R)-2-(1R)-3,3-Diffluorocyclopentyl-2-hydroxyphenylacetamide Structures. Part 2, Bioorganic & Medicinal Chemistry Letters, 2003, pp. 2167-2172, vol. 13, Elsevier, ., US.
Search Report and Written Opinion in PCTEP2016057569, dated May 20, 2016, WO.
Search Report and Written Opinion in PCTEP2016057580, dated Jul. 20, 2016.
Search Report in EP15165365, dated Oct. 2, 2015, EP.
Search Report in EP15165368, dated Aug. 11, 2015.
Written Opinion 2 in PCTEP2016057569, dated Mar. 3, 2017.
Written Opinion in EP15165365, dated Oct. 2, 2015, EP.
Written Opinion in EP15165368, dated Aug. 11, 2015.
2-cyclohexyl-2-hydroxy-N-methyl-2-[henyl-N-(2-piperidin-1-ylethyl)acetamide, PubChem Database, 2011, pp. 1-6; XP55284000.
Written Opinion 2 in PCTEP2016057580.
Carceller et al., (Pyridylcyanomethyl)piperazines as Orally Active PAF Antagonists, Journal of Medicinal Chemistry, 1992, pp. 4118-4134, vol. 35 No. 22.
Grande et al., Keratin ocyte Muscarinic Acetylcholine Receptors: Immunolocalization and Partial Characterization, Journal of Investigative Dermatology, 1995, pp. 95-100, vol. 104 No. 1, Elsevier.
Hromatka et al., The Synthesis of new acylpiperazines, Monatshefte Fuer Chemie, 1954, pp. 1208-1214; no translation avail., vol. 85 Iss 6, DE.
IPRP2 in PCTEP2016057569, May 30, 2017.
IPRP2 in PCTEP2016057580, Jun 19, 2017.
Kurzen et al, The Non-neuronal Cholinergic System of Human Skin, Hormone and Metabolic Research, 2007, pp. 125-137, vol. 39.
Levine et al, The Physiological Disposition of Oxyphenonium Bromide (Antrenyl) and Related Compounds, Journal of Pharmacology and Experimental Therapeutics, 1957, pp. 63-70; XP009186280, vol. 121, No. 1, DE.
Margulis et al., E-cadherin Suppression Accelerates Squamous Cell Carcinoma Progression in Three-Dimensional, Human Tissue Constructs, Cancer Research, 2005, pp. 1783-1791, vol. 65 Issue 5.
Mitsuya et al., A Potent, Long-Acting, Orally Active (2R)-2-[1R)-3,3-Difluorocyclopentyl]-2-hydroxy-2-phenylacetamide: A Novel Muscarinic M3 Receptor Antagonist with High Selectivity for M3 over M2 Receptors, Journal of Medicinal Chemistry, 2000, pp. 5017-5029; XP002547105, vol. 43 No. 26, US.
Ndoye et al, Identification and mapping of keratinocyte muscarinic acetylcholine receptor subtypes in human epidermis, Journal of Investigative Dermatology, 1998, pp. 410-416, vol. 111.
Nguyen et al., Synergistic control of keratinocyte adhesion through muscarinic and nicotinic acetylcholine receptor subtypes, Experimental Cell Research, 2004, pp. 534-549, vol. 294, Elsevier.
Ogino et al., Muscarinic M3 Receptor Antagonists with (2R)-2-(1R)-3,3-Difluorocyclopentyl-2-hydroxyphenylacetamide Structures. Part 2, Bioorganic & Medicinal Chemistry Letters, 2003, pp. 2167-2172, vol. 13, Elsevier, ., US.
R. M. Eglen, Muscarinic receptor subtypes in neuronal and non-neuronal cholinergic function, Autonomic and Autacoid Pharmacology, 2006, pp. 219-233; XP008078365, vol. 26, No. 3, GB.
Saturnino et al, Amide derivatives with H1-antihistaminic effect, Pharmaceutica Acta Helvetiae, 1998, pp. 279-283; XP055217106, vol. 72, No. 5, IT.
Search Report and Written Opinion in PCTEP2016057569, May 20, 2016, WO.
Search Report and Written Opinion in PCTEP2016057580, Jul. 20, 2016.
Search Report in EP15165365, Oct. 2, 2015, EP.
Search Report in EP15165368, Aug. 11, 2015.
Smith et al, Physiologically Active Compounds. III. Hydrochlorides of Amino Esters of Phenylcyclohexylglycolic Acids . . ., The Journal of Organic Chemistry, 1951, pp. 1301-1309; XP000985827, vol. 24, US.
Written Opinion 2 in PCTEP2016057569, Mar. 3, 2017.
Written Opinion in EP15165365, Oct. 2, 2015, EP.
Written Opinion in EP15165368, Aug. 11, 2015.
Zha et al., Synthesis and Structure-Activity Relationship Studies for Hydantoins and Analogues as Voltage-Gated Sodium Channel Ligands, Journal of Medicinal Chemistry, Apr. 1, 2004, pp. 6519-6538, vol. 47 No. 26.
De Paco et al.; Farmaco, Edizione Scientifica; Derivatives of ethylphenylacetic acid I; 540-548; no translation available; vol. 11; Pavia: Societa chimica italiana.

* cited by examiner

N-ARALKYLCARBONYLDIAMINE COMPOUNDS AND PERSONAL CARE COMPOSITIONS COMPRISING THE SAME

FIELD OF THE INVENTION

The present invention relates to novel N-aralkylcarbonyldiamine compounds and personal care compositions comprising one or more of said compounds.

BACKGROUND OF THE INVENTION

Young and healthy looking skin is a desirable attribute worldwide and the market for cosmetic products capable of improving our skin appearance is significant and growing. As we age, our natural ability to maintain young and healthy looking skin diminishes and, consequently, our skin appearance changes in response to the biological processes that take place within the skin at the cellular level. Modulation of these processes at the skin surface via intervention of specific pathways with diverse cosmetic ingredients can improve skin health and appearance. Numerous examples of how cosmetic ingredients can modulate appearance via this type of intervention are well documented.

Increased cell proliferation and migration, as well as epidermal thickness are some of the traits associated with a younger and healthy looking skin phenotype. Among the various pathways leading to such traits, inhibition of the muscarinic cholinergic system, particularly the muscarinic 3 receptor, has been shown to increase cell proliferation and migration in healthy skin. See for example, in Grando et al., "Keratinocyte muscarinic acetylcholine receptors: immunolocalization and partial characterization" Journal of Investigative Dermatology (1995), 104, 95-100; Ndoye et al. "Identification and mapping of keratinocyte muscarinic acetylcholine receptor subtypes in human epidermis" Journal of Investigative Dermatology (1998) 111, 410-416; Nguyen et al "Synergistic control of keratinocyte adhesion through muscarinic and nicotinic acetylcholine receptor subtypes" Exp. Cell. Res. (2004) 294, 534-549; Kurzen et al. "The non-neuronal cholinergic system of human skin" Horm. Metab. Res. (2007) 39, 125-137.

Muscarinic receptor antagonists have been claimed in medications used to treat skin diseases. For example, WO0110427 describes the use of anti-muscarinic agents to treat skin disorders including psoriasis, atopic dermatitis, eczema, urticaria, acne, etc. WO09068876 describes the use of muscarinic receptor antagonists with antibacterial and sebum suppressive activities in the manufacture of medicaments to treat bacterial skin infections. Further, WO09150408 and WO09068876 describe the use of muscarinic receptor antagonists in compositions to treat acne and seborrhea, for example.

Various compositions comprising some N-aralkylcarbonyldiamines or related structures have been described, for example in U.S. Pat. No. 5,192,779 (Fujisawa Pharmaceutical Co.) and Smith et al., "Physiologically active compounds. III. Hydrochlorides of amino esters of phenylcuclohexylglycolic acids, of amides of benzilic, phenylcyclohexyl- and dicyclohexylglycolic, and phenylcyclohexylacetic acids; 2-methylthioethyl ester methiodides of substituted benzilic acids", Journal of Organic Chemistry (1959) 1301-1309. However the specific derivatives used are different from the compounds of our invention. Moreover, none of these compositions are recognized for use as cosmetics for personal care benefits.

It is also noted that compounds of the invention differ from many somewhat related compounds in that compounds comprising primary amines, secondary amines and secondary amides (defined as compounds containing a —CONH— functional group) are not included in the scope of our compounds.

The novel N-aralkylcarbonyldiamine compounds of the invention have several advantages for personal care compositions compared to N-aralkylcarbonyldiamines and muscarinic receptor antagonists described in the prior art. For example, compounds of the invention are not quaternized, which distinguishes them from some of the currently used muscarinic receptor antagonists, for example oxyphenonium bromide, glycopyrrolate, ipatropium, tiotropium to name a few. By "not quaternized" is meant that they do not have an additional bond attaching an alkyl group to the nitrogen atom of the tertiary amine which provides a permanent positive charge. Quaternized compounds are less desirable because they do not penetrate skin as effectively compared to when they are in an unquaternized form. The novel unquaternized N-aralkylcarbonyldiamines are therefore better suited for skin applications. Further, the inventive compounds do not contain ester functional groups, unlike many of the currently used muscarinic receptor antagonists such as oxybutynin, oxyphenonium bromide, hyoscyamine, dicyclomine, propiverine to name a few. Compounds with ester groups are less desirable for skin compositions since they are prone to hydrolysis once formulated, especially under high heat storage conditions. The compounds of the invention contain tertiary amide bonds which are known to be more stable than their corresponding esters.

SUMMARY OF THE INVENTION

The present invention is based at least in part on the finding that certain novel N-aralkylcarbonyldiamines (Structure I below) are effective at inhibiting the muscarinic 3 receptor and increasing cell proliferation, thereby providing cosmetic benefits for personal care. The invention further relates to personal care compositions, preferably anti-aging compositions, comprising the novel N-aralkylcarbonyldiamine compounds of Structure I. The compositions of the invention may comprise one or more N-aralkylcarbonyldiamine. The invention also provides methods of enhancing cell proliferation, enhancing cell migration, and increasing epidermal thickness, all traits associated with younger, healthy skin and improving personal care. The method comprises applying to a person desirous of, or in need of, such enhanced cell attributes a composition comprising the novel compounds of the invention. The composition may be applied in the form of a liquid, lotion, fluid cream, cream, gel, serum, paste, foam, spray, aerosol, roll-on, stick, solid, soft solid and/or any other cosmetically acceptable carrier for skin

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

Unless indicated otherwise, all percentages for amount or amounts of ingredients used are to be understood to be percentage by weight.

The disclosure of the invention as found herein is to be considered to cover all embodiments as found in the claims as being multiply dependent upon each other irrespective of the fact that claims may be found without multiple dependency or redundancy.

N-Aralkylcarbonyldiamines

Novel N-aralkylcarbonyldiamines of the invention have Structure I as set forth below:

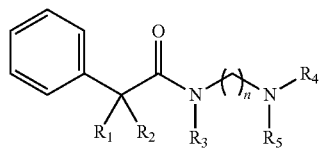

I wherein n=2 or 3,
wherein when n=2, 3, $R_1$ is selected from hydrogen or hydroxyl, $R_2$ is selected from cyclohexyl or cyclopentyl, $R_3$ is selected from the group consisting of $C_1$-$C_3$ alkyl, and $R_4$ and $R_5$ are selected from the group consisting of $C_1$-$C_6$ alkyl, wherein said alkyl group may be linear, cyclic or branched with the proviso that when $R_2$ is cyclohexyl, $R_1$ and $R_3$ cannot be hydrogen and $C_1$ alkyl, respectively and simultaneously; and with the further proviso that, when $R_2$ is cyclohexyl, $R_1$ and $R_3$ cannot be hydrogen and $C_1$ to $C_2$ alkyl, respectively and simultaneously; and when $R_2$ is cyclopentyl, $R_1$ and $R_3$ cannot be hydrogen and $C_2$ alkyl, respectively and simultaneously.

In a preferred combination, n=2, $R_1$ is hydroxyl, $R_2$ is cyclopentyl, $R_3$ is $C_1$ to $C_3$ alkyl, preferably methyl and both $R_4$ and $R_5$ are $C_1$ to $C_3$ alkyl, preferably both are methyl.

In another preferred combination, n=2, $R_1$ is hydroxyl, $R_2$ is cyclohexyl, $R_3$ is $C_1$ to $C_3$ alkyl, preferably methyl and both $R_4$ and $R_5$ are $C_1$ to $C_3$ alkyl, preferably both are methyl.

It will be understood that amine salts (e.g., halogen salts, tosylates, mesylates, carboxylates (e.g., $C_2$ to $C_{12}$ alkylcarboxylates which may be linear, branched or cyclic; and saturated or unsaturated), hydroxides and any other counterions used in, for example, cosmetic industry) of the compound of Structure I are also considered to be covered by the structure). Salt formation helps provide isolation and purification benefits prior to formulation. During formulation, the salt form can be changed and optimized for maximum delivery.

As indicated above, primary and secondary amines, i.e. $R_4$ and $R_5$ representing hydrogen and alkyl groups, respectively, as well as secondary amides, i.e. $R_3$ representing a hydrogen atom, are not included within the scope of the invention.

Quaternary ammonium compounds, i.e. containing a permanently charged nitrogen, are also not included within the scope of the invention. Quaternary compounds are not desirable because it is difficult to achieve effective skin penetration for such quaternary ammonium compounds.

Amounts of the substituted N-aralkylcarbonyldiamine in compositions of the invention may range from 0.001% to 20%, preferably from 0.01 to 10%, more preferably from 0.1 to about 10%, optimally from 0.1 to about 5% by weight of the composition. The compositions comprise one or more N-aralkylcarbonyldiamine.

Reagents & Analytical Methods

All reagents and solvents were obtained from commercial sources (Sigma-Aldrich, EMD Chemicals) and used without further purification unless otherwise indicated. Parallel reactions and parallel solvent removal were performed using a Buchi Syncore reactor (Buchi Corporation, New Castle, Del.). Reaction monitoring was performed using thin layer chromatography (TLC). TLC was performed using silica gel 60 F254 plates (EMD Chemicals) and visualizing by UV (254 nm), 4% phosphomolybdic acid (PMA) in ethanol (EtOH), 4% ninhydrin in EtOH and/or using an iodine chamber. Flash chromatography (FC) was performed using a Biotage SP4 system (Biotage LLC, Charlottesville, Va.). High performance liquid chromatography (HPLC) was performed using a Waters 2695 Separations Module equipped with a Waters 2996 Photodiode Array Detector and operated with Empower Pro software (Waters Corp.). Separations were carried out at 1 ml/min on a Restek Pinnacle DB C18 column (5 um, 4.6×150 mm) maintained at 30° C. Samples for HPLC were prepared by dissolving sample in mobile phase A:B (1:1) (1 mg/ml) and injecting 5-10 μL onto the column. The mobile phase consisted of A=0.1% trifluoroacetic acid (TFA) in water and B=0.1% TFA in acetonitrile (ACN) operated using gradient elution from 95:5 A:B to 5:95 A:B (gradient, 25 min) followed by 100% B (isocratic, 5 min). Gas Chromatography (GC) was performed using an Agilent 7890A Gas Chromatograph equipped with an Agilent DB-5HT (15m×0.32 mm; 0.1u) column and an FID detector heated @ 325° C. Samples were prepared at 25 ppm concentrations in acetone and the injection volume was 1 uL. The air, helium and hydrogen flows were maintained @ 400, 25 and 30 ml/min and the separation gradient consisted of 100° C. (isothermal, 1 min), 15° C./min up to 250° C., 250° C. (isothermal, 4 min), 25° C./min up to 300° C., and 300° C. (isothermal, 3 min). Liquid chromatography/mass spectrometry (LC-MS) was performed using a Finnigan Mat LCQ Mass Spectrometer via direct infusion of samples (50 ppm) in methanol and the total ion count monitored using electrospray ionization in the (+) mode (ESI+). Proton ($^1$H) and Carbon ($^{13}$C) nuclear magnetic resonance (NMR) spectroscopy was performed using a Eft-60 NMR Spectrometer (Anasazi instruments, Inc.) and processed using WinNuts software (Acorn NMR, Inc.). Melting points were determined using a Meltemp apparatus (Laboratory Devices). Purity was determined by HPLC-UV/Vis and/or GC. All compounds were unequivocally confirmed by LC-MS and/or 1H NMR.

Reaction Scheme I

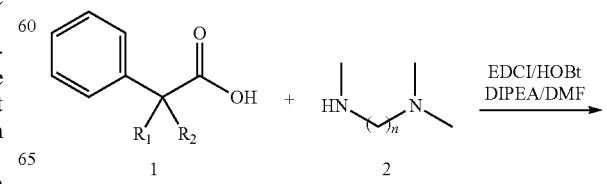

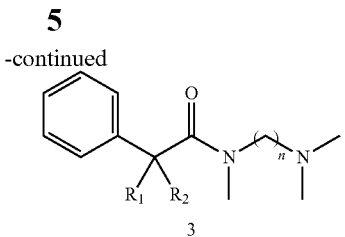

| Structure ID | $R_1$ | $R_2$ | n | Purification Solvents[a] | Purity (%)[b] | LC-MS (M + H)[c] |
|---|---|---|---|---|---|---|
| 3a | cyclopentyl | OH | 2 | 5% M in C | 97.0 | 305.4 |
| 3b | cyclopentyl | OH | 3 | 8% M in C | 99.5 | 319.5 |
| 3c | cyclopentyl | H | 2 | 5% M in C | 99.5 | 289.4 |
| 3d | cyclohexyl | OH | 2 | 5% M in C | 98.2 | 319.4 |

[a]All compounds purified by FC on silica gel. M = methanol; C = chloroform.
[b]Purity determined by HPLC-UV.
[c]Expressed as [M + H]+ mass observed @ 100% abundance.

General Procedure I: Amines (1.0 equivalents) were added to solutions of carboxylic acid (1.0 equivalents), hydroxybenzotriazole (HOBt) (1.25 equivalents) and 1-ethyl-3-(3-dimethylaminopropyl)carbodiimide) (EDCI) (1.05 equivalents) in dimethylformamide (DMF) (0.7M solution), followed by diisopropylethylamine (DIPEA) (1.0 equivalents) and the mixture stirred at RT for 16 h. The reactions were monitored by TLC using methanol:chloroform (MeOH:CHCl$_3$) mixtures and PMA staining until substantial amount of product was observed. The solutions were partitioned between 15% isopropyl alcohol (IPA) in CHCl$_3$: 1N NaOH (5 vol:5 vol) and the organic layer dried with sodium sulfate (Na$_2$SO$_4$), filtered and the solvents removed in vacuo. The crude products were purified by FC on silica gel using suitable solvent mixtures of MeOH:CHCl$_3$ depending on TLC conditions. Product purity was determined by HPLC and product identity confirmed by LC-MS (ESI+) and $^1$H NMR.

Evaluation of N-Aralkylcarbonyldiamines
Muscarinic 3 Receptor Binding Assay

The muscarinic 3 receptor binding assay was adapted from Perkin Elmer. Briefly, assay buffer (60 μL of pH 7.4 phosphate saline buffer) was added to polypropylene round bottom 96-well microtiter plates, followed by CHO cell suspension expressing the human M3 receptor (1 mg suspension/ml; 20 ug membrane suspension per well). $^3$H-Scopolamine (20 μL of a 7.5 nM solution) was added to each well and plates were shaken at room temperature for 2h. Atropine (Sigma-Aldrich, St. Louis, Mo.) was used as a positive control. Test compounds and control samples were prepared in DMSO (20 mM) and diluted to give a final concentration of 20 μM. The reaction mixtures were then added to matrix 96-well GFC filtration microtiter plates that had been previously pretreated with 0.5% polyethylimine (100 μL) for 4h and filtered. The binding reactions were terminated by filtering through the GFC plates and washing & filtering with ice-cold phosphate saline buffer (5×100 μL). Once the filters were dry, microscint scintillation cocktail (100 μL) was added to each well, allowed to sit for 20 min and the plates analyzed using a TopCount scintillation counter. Test compounds which showed >50% reduction in $^3$H-scopolamine binding at a final concentration of 20 μM were subjected to further serial dilutions and evaluated at various concentrations to determine their IC$_{50}$ value. Curve fitting of % inhibition versus concentration using Excell software allowed determination of IC$_{50}$ values for test compounds. The IC$_{50}$ value is the concentration of compound needed to inhibit the muscarinic receptor response by 50% of its maximum response. As the 1050 value for a compound decreases below 10 μM, its antagonistic potency against the muscarinic 3 receptor increases, which means less of the compound is needed to inhibit the receptor effectively. This thus leads, as noted, to enhanced cell proliferation, enhanced cell migration, etc.

Use of 10 μM to show effect was based on the fact that applicants had identified internally a muscarinic 3 receptor antagonist with IC$_{50}$ of 10 μM which demonstrated both increased epidermal thickness and increased cell proliferation.

It should be noted that Ki-67 assay (discussed below) is a quantification assay associated with cell proliferation (higher the number of Ki67 positive cells when treated with compound, the higher the cell proliferation rate (associated with young healthy skin)), there is no necessary correlation between IC$_{50}$ value and cell proliferation. This is because the muscarinic pathway (used for IC$_{50}$ test) is not the only pathway associated with cell proliferation. So there is no guarantee that inhibition of the pathway that leads to IC$_{50}$<10 μM necessarily leads to cell proliferation. For example, a potent inhibitor of the muscarinic pathway (low IC$_{50}$) may hit other pathways which reduce cell proliferation. Further, there are various muscarinic receptor subtypes which may regulate in different ways. One compound may be a potent inhibitor of the muscarinic 3 receptor (which should enhance cell proliferation), but also be a potent receptor inhibitor of muscarinic 1, 2, 4 or 5 receptor, and this might counter the response and lead to less or no cell proliferation.

Ki-67 Assay Using Human Living Skin Equivalents

The living skin equivalents (LSE) were processed as described by Margulis et al. "E-cadherin suppression accelerates squamous cell carcinoma progression in three-dimensional, human tissue constructs", Cancer Research (2005), 65, 1783-1791. The cultures were prepared using a human neonatal fibroblast donor and a human aged primary keratinocyte donor from Cascade Biologics (Portland, Oreg.). Briefly, each dermal matrix was prepared from fibroblasts (75K, P3) seeded in collagen and grown for 1 wk in medium 106 (Cascade M106-500). The aged keratinocytes (P3) were added to the matrix at 275-300 K cells per insert and grown for 3d submerged in JG-I media and exchanged for JG-II media on the third day, followed by air exposure 2d later. At this point, the JG-II media was exchanged for JG-AL media until the end of the experiment. Four days after air exposure, samples were split into quadruplicate groups. LSE cultures were either left untreated, vehicle treated (0.1% DMSO) or dosed with test compounds delivered once per day for 4 d. At 8 d post air exposure, a 6 mm biopsy from each culture was taken and processed for immunohistochemistry (IHC). Briefly, each biopsy was fixed for 3 h in neutral buffered formalin, transferred into ethanol (70%) and processed (tissue processing, embedding and sectioning) by AML labs (Baltimore, Md.). All precut sections were prepared for IHC using the Superpicture IHC kit (Invitrogen, Carlsbad, Calif.). Primary rabbit polyclonal Ki-67 antibody (Thermo Scientific, RB-9043-P, 1:1000) was used as per manufacturer's instructions. Slides were counterstained with haematoxylin and mounted with ClearMount water-soluble mounting medium (Invitrogen, Carlsbad, Calif.). Automated IHC processing for Ki-67 (MACH4 AP) was performed on the Intellipath FLX (Biocare Medical). Slides were cleared in xylene and rehydrated in descending alcohols and brought to water. High heat epitope retrieval was performed by immersing the slides in a citrate buffer and then placing in a decloaking chamber (Biocare Medical). All subsequent steps were performed on the Intellipath FLX. Blocking, prode and polymer incubation was performed for 10 minutes. Slides were incubated with Ki-67 (Thermo Fischer) for 1h at a 1:10,000 dilution. The chromagenic stain, Vuclan Fast Red (Biocare Medical) was added to the slides and incubated for 15 min. The slides were then removed from the instrument, rinsed with water, dried in a 60° C. over for 1h and placed in xylene and coverslipped. The number of proliferation positive cells (Ki-67 positive) in the basal layer for all samples were determined by enlarging all images to the same size, standardizing the sample area by drawing identical rectangular boxes encompassing the basal layer showing Ki-67 antibody staining and counting the cells using image photography with a 20× objective. The greater the number, the greater the proliferation. All data was analyzed for significance using the t-tests to generate p-values (p-values<0.01 represent 99% confidence, p values of 0.05 represent 95% confidence both of which are statistically significant). Results were expressed as % increase of Ki-67 stained positive cells over vehicle (0.1% DMSO).

Compositions

Cosmetically Acceptable Carrier

Compositions of the invention also comprise a cosmetically acceptable vehicle dilutant, dispersant, or carrier for the active components in order to facilitate their distribution when the composition is applied to the skin.

Amounts of the carrier may range from about 1 to about 99.9%, preferably from about 70 to about 95%, optimally from about 80 to about 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W type or multiple emulsions of the W/O/W or O/W/O variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, natural or synthetic esters, hydrocarbons, alcohols and fatty acids. Amounts of the emollients may range anywhere from about 0.1 to about 95%, preferably between about 1 and about 50% by weight of the composition.

Silicone oils may be divided into the volatile and non-volatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 5 to 6, silicon atoms.

Non-volatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about $5 \times 10^{-6}$ to 0.1 m$^2$/s at 25° C. Among the preferred non-volatile emollients useful in the present compositions are the polydimethyl siloxanes having viscosities from about $1 \times 10^{-5}$ to about $4 \times 10^{-4}$ m$^2$/s at 25° C.

Another class of non-volatile silicones are emulsifying and non-emulsifying silicone elastomers. Representative of this category is DimethiconeNinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
a) Alkyl esters of saturated fatty acids having 10 to 24 carbon atoms. Examples thereof include behenyl neopentanoate, isononyl isonanonoate, isopropyl myristate and octyl stearate.
b) Ether-esters such as fatty acid esters of ethoxylated saturated fatty alcohols.
c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
d) Wax esters such as beeswax, spermaceti wax and tribehenin wax.
e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions. Hydrocarbons which are suitable cosmetically acceptable carriers include petrolatum, mineral oil, $C_{11}$-$C_{13}$ isoparaffins, polybutenes and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids and mixtures thereof.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol and mixtures thereof.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 13820), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Preferred are emollients that can be used, especially for products intended to be applied to the face, to improve sensory properties and are chosen from the group of oils that do not form stiff gels with compounds of the invention; these include polypropylene glycol-14 butyl ether otherwise known as Tegosoft PBE, or PPG15 stearyl ether such as Tegosoft E, other oils such as esters, specifically, isopropyl myristate, isopropyl palmitate, other oils could include castor oils and derivatives thereof.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Skin moisturizers, e.g. hyaluronic acid and/or its precursor N-acetyl glucosamine may be included. N-acetyl glucosamine may be found in shark cartilage or shitake mushrooms and are available commercially from Maypro Industries, Inc (New York). Other preferred moisturizing agents include hydroxypropyl tri($C_1$-$C_3$ alkyl)ammonium salts. These salts may be obtained in a variety of synthetic procedures, most particularly by hydrolysis of chlorohydroxypropyl tri($C_1$-$C_3$ alkyl)ammonium salts. A most preferred species is 1,2-dihydroxypropyltrimonium chloride, wherein the $C_1$-$C_3$ alkyl is a methyl group. Amounts of the salt may range from about 0.2 to about 30%, and preferably from about 0.5 to about 20%, optimally from about 1% to about 12% by weight of the topical composition, including all ranges subsumed therein.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

Still other preferred moisturizing agents which may be used, especially in conjunction with the aforementioned ammonium salts include substituted urea like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-dihydroxyethyl urea; N,N'-di-hydroxypropyl urea; N,N,N'-trihydroxyethyl urea; tetra(hydroxymethyl) urea; tetra (hydroxyethyl) urea; tetra(hydroxypropyl urea; N-methyl, N'-hydroxyethyl urea; N-ethyl-N'-hydroxyethyl urea; N-hydroxypropyl-N'-hydroxyethyl urea and N,N'dimethyl-N-hydroxyethyl urea. Where the term hydroypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea that may be used in the topical composition of this invention range from about 0.01 to about 20%, and preferably, from about 0.5 to about 15%, and most preferably, from about 2 to about 10% based on total weight of the composition and including all ranges subsumed therein.

When ammonium salt and/or substituted urea are used, in a most especially preferred embodiment at least from about 0.01 to about 25%, and preferably, from about 0.2 to about 20%, and most preferably, from about 1 to about 15% humectant, like glycerine, is used, based on total weight of the topical composition and including all ranges subsumed therein.

Form of the Composition

The compositions of the present invention may be formulated as lotion, fluid cream, cream, gel, serum, spray, roll-on, stick. They may be solids or soft-solids as well. In preferred "non-solidness" form, compositions have viscosity, e.g. as measured using a Brookfield DV-I+viscometer (20 RPM, RV6, 30 seconds), which in general is in the range of from 1 Pas to 500 Pas, preferably from 1 Pas to 200 Pas, more preferably from 2 Pas to 100 Pas, most preferably from 3 Pas to 50 Pas (measured at room temperature).

Preferably, compositions of the invention are leave-on compositions. That is, they are intended to be applied to remain on the skin. These leave-on compositions are to be distinguished from compositions which are applied to the skin and subsequently removed either by washing, rinsing, wiping, or the like either after or during the application of the product. Surfactants typically used for rinse-off compositions have physico-chemical properties giving them the ability to generate foam/lather in-use with ease of rinse; they can consist of mixtures of anionic, cationic, amphoteric, and nonionic. Surfactants used in leave-on compositions on the other hand are not required to have such properties. Rather, as leave-on compositions, they are not intended to be rinsed-off, they need to be non-irritating, and therefore it is desirable to minimize the total level of surfactant and the total level of anionic surfactant in skin leave-on compositions. Therefore, the compositions of the present invention preferably contain, with respect to surfactants, predominantly nonionic surfactants. The anionic surfactants are present in an amount of at most 5%, preferably from 0.01 to 4%, more preferably from 0.01 to 3%, most preferably from 0.01 to 2% and optimally are substantially absent (less than 1%, preferably less than 0.1%, or even less than 0.01%). Salts of N-aralkylcarbonyldiamines are not considered anionic surfactants herein. Also, while salts of alkylcarboxylate may or may not be considered as anionic surfactants, their use is typically desirable in leave-on compositions and so need not be minimized. The total level of surfactant in the inventive compositions is preferably no more than 10%, more preferably below 8%, most preferably at most 5%.

The compositions of the present invention are typically in the form of emulsions, which may be oil-in-water, or water-in-oil; preferably the compositions are oil-in-water emulsions. Another preferred format is a cream, furthermore preferably one which has a vanishing cream base. Vanishing cream base is one which comprises 5 to 40% fatty acid and 0.1 to 20% soap. In such creams, the fatty acid is preferably substantially a mixture of stearic acid and palmitic acid and the soap is preferably the potassium salt of the fatty acid mixture, although other counterions and mixtures thereof can be used. The fatty acid in vanishing cream base is often prepared using hystric acid which is substantially (generally about 90 to 95%) a mixture of stearic acid and palmitic acid. A typical hystric acid comprises about 52-55% palmitic acid and 45-48% stearic acid of the total palmitic-stearic mixture. Thus, inclusion of hystric acid and its soap to prepare the vanishing cream base is within the scope of the present invention. It is particularly preferred that the composition comprises higher than 7%, preferably higher than 10%, more preferably higher than 12% fatty acid.

Optional Ingredients

Compositions of the invention may be used to deliver a variety of skin conditioning benefits. "Conditioning" as used herein includes prevention and treatment of aged and photo-damaged skin, appearance of wrinkles, age spots, aged skin, increasing skin firmness, increasing stratum corneum flexibility, lightening skin color, controlling sebum excretion and generally increasing the quality and radiance of skin. The composition may be used to improve fibroblast metabolic activity and proliferation, skin desquamation and epidermal differentiation and improve skin appearance or general aesthetics.

Preferably the pH of the inventive compositions is less than about 8, more preferably is in the range of from 3.5 to 8.0, most preferably is from 5 to 7.8. N-aralkylcarbonyldiamine compound(s) are preferably included in the inventive compositions in an amount of from 0.001 to 20%, more preferably from 0.01 to 10%, most preferably from 0.1 to 10%, and optimally from 0.1 to 5%. The amounts of the compound(s) or salts thereof are not meant to be included within the surfactants amounts herein.

Surfactants

Total concentration of the surfactant when present may range from about 0.1 to about 90%, preferably from about 1 to about 40%, optimally from about 1 to about 20% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Useful amphoteric surfactants include cocoamidopropyl betaine, $C_{12}$-$C_{20}$ trialkyl betaines, sodium lauroamphoacetate, and sodium laurodiamphoacetate.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof. In compositions containing N-aralkylcarbonyldiamines, the preferred surfactants are high HLB nonionic sugar surfactant with an HLB of at least 7 selected from the group consisting of alkyl polyglucosides, sugar fatty acid esters, aldobionamides, polyhydroxy fatty acid amides and mixtures thereof.

Rheology Modifier

A rheology modifier may be included and is selected from the group consisting of silica such as fumed silica or hydrophilic silicas and clays such as magnesium aluminum silicate, betonites, hectorite, laponite, and mixtures thereof. A rheology modifier is employed in an amount of from 0.01 to 2%, preferably from 0.05 to 1%.

Skin Benefit Ingredients

The inventive composition preferably includes an additional skin lightening compound, to obtain optimum skin lightening performance at an optimum cost. Illustrative substances are placental extract, lactic acid, niacinamide, arbutin, kojic acid, ferulic acid, hydroquinone, resorcinol and derivatives including 4-substituted resorcinols and combinations thereof. More preferably such additional skin lightening compound is a tyrosinase inhibitor to complement the melanogenesis inhibition activity of the substituted monoamines, most preferably a compound selected from the group consisting of kojic acid, hydroquinone and 4-substituted resorcinol. Also dicarboxylic acids represented by the formula HOOC—(CxHy)—COOH where x=4 to 20 and y=6 to 40 such as azelaic acid, sebacic acid, oxalic acid, succinic acid, fumaric acid, octadecenedioic acid or their salts or a mixture thereof, most preferably fumaric acid or salt thereof, especially di-sodium salt. A combination of hydroxyl stearic acid (12-HSA) with fumaric acid or salts thereof is preferred, especially for skin lightening formulations. Amounts of these agents may range from about 0.1 to about 10%, preferably from about 0.5 to about 2% by weight of the composition. It is preferred that the skin lightening coactive according to the invention is vitamin B3 or a derivative thereof and is selected from the group consisting of niacinamide, nicotinic acid esters, non-vasodilating esters of nicotinic acid, nicotinyl amino acids, nicotinyl alcohol esters of carboxylic acids, nicotinic acid N-oxide, niacinamide N-oxide and mixtures thereof.

Sunscreen is another preferred ingredient of the inventive compositions. Particularly preferred are such materials as ethylhexyl p-methoxycinnamate (available as Parsol MCX®), Avobenzene (available as Parsol 1789®), octylsalicylate (available as Dermablock OS®), tetraphthalylidene dicamphor sulfonic acid (available as Mexoryl SX®), benzophenone-4 and benzophenone-3 (Oxybenzone). Inorganic sunscreen actives may be employed such as microfine titanium dioxide, zinc oxide, polyethylene and various other polymers. By the term "microfine" is meant particles of average size ranging from about 10 to about 200 nm, preferably from about 20 to about 100 nm. Amounts of the sunscreen agents when present may generally range from 0.1 to 30%, preferably from 2 to 20%, optimally from 4 to 10% by weight of the composition.

More preferred inventive compositions include both the additional skin lightening compound, especially tyrosinase inhibitor, and a sunscreen compound.

Another preferred ingredient of the inventive compositions is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120 issued Jun. 30, 1987 to Parish et al.; U.S. Pat. No. 4,885,311 issued Dec. 5, 1989 to Parish et al.; U.S. Pat. No. 5,049,584 issued Sep. 17, 1991 to Purcell et al.; U.S. Pat. No. 5,124,356 issued Jun. 23, 1992 to Purcell et al.; and U.S. Pat. No. Reissue 34,075 issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The retinoid is preferably substantially pure, more preferably essentially pure. The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is preferably used in an amount of from or about 0.01% to or about 0.15%; retinol esters are preferably used in an amount of from or about 0.01% to or about 2% (e.g., about 1%); retinoic acids are preferably used in an amount of from or about 0.01% to or about 0.25%; tocopheryl-retinoate, adapalene, and tazarotene are preferably used in an amount of from or about 0.01% to or about 2%.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may include vitamins. Illustrative vitamins are Vitamin A (retinol), Vitamin B2, Vitamin B3 (niacinamide), Vitamin $B_6$, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. A particularly suitable Vitamin $B_6$ derivative is Pyridoxine Palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001 to 10%, preferably from 0.01% to 1%, optimally from 0.1 to 0.5% by weight of the composition.

Another type of useful substance can be that of an enzyme such as oxidases, proteases, lipases and combinations. Particularly preferred is superoxide dismutase, commercially available as Biocell SOD from the Brooks Company, USA.

Desquamation promoters may be present. Illustrative are the monocarboxylic acids. Monocarboxylic acids may be substituted or unsubstituted with a carbon chain length of up to 16. Particularly preferred carboxylic acids are the alpha-hydroxycarboxylic acids, beta-hydroxycarboxylic or poly-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic malic and tartaric acids. A representative salt that is particularly preferred is ammonium lactate. Salicylic acid is representative of the beta-hydroxycarboxylic acids. Amounts of these materials when present may range from about 0.01 to about 15% by weight of the composition. Other phenolic acids include ferulic acid, salicylic acid, kojic acid and their salts.

A variety of herbal extracts may optionally be included in compositions of this invention. Illustrative are pomegranate, white birch (*Betula Alba*), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as resveratrol, alpha-lipoic acid, ellagic acid, kinetin, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

The compositions of the present invention may contain a safe and effective amount of a peptide active selected from pentapeptides, derivatives of pentapeptides, and mixtures thereof. As used herein, "pentapeptides" refers to both the naturally occurring pentapeptides and synthesized pentapeptides. Also useful herein are naturally occurring and commercially available compositions that contain pentapeptides. A preferred commercially available pentapeptide derivative-containing composition is Matrixyl™, which is commercially available from Sederma, France. The pentapeptides and/or pentapeptide derivatives are preferably included in amounts of from about 0.000001% to about 10%, more preferably from about 0.000001% to about 0.1%, even more preferably from about 0.00001% to about 0.01%, by weight of the composition. In embodiments wherein the pentapeptide-containing composition Matrixyl™ is used, the resulting composition preferably contains from about 0.01% to about 50%, more preferably from about 0.05% to about 20%, and even more preferably from about 0.1% to about 10%, by weight of the resulting composition of Matrixyl™.

Additional peptides, including but not limited to, di-, tri-, and tetrapeptides and derivatives thereof, and poly amino acid sequences of molecular weight from 200-20000. Amino acids may be naturally occurring or synthetic, dextro or levo, straight chain or cyclized and may be included in the compositions of the present invention in amounts that are safe and effective. As used herein, "peptides" refers to both the naturally occurring peptides and synthesized peptides. Also useful herein are naturally occurring and commercially available compositions that contain peptides.

Suitable dipeptides for use herein include Carnosine. Preferred tripeptides and derivatives thereof may be purchased as Biopeptide CL™. and a copper derivative sold commercially as lamin, from Sigma (St. Louis, Mo.).

Further ingredients useful in skin care compositions herein may be selected from any and all: skin conditioning agents, skin feel mildness agents, suspending agents, auxiliary thickening agents, viscosity control agents, dispersants, solubilizing/clarifying agents, stabilizers, opacifiers/pearlescent agents, chelating/sequestering agents, hydrotropes, bactericides/fungicides, antioxidants, pH control agents, buffering agents, colorants and perfumes/fragrances, water, other optional ingredients (auxiliary agents) and the like.

The compositions of the present invention can also be optionally, incorporated into a water insoluble substrate for application to the skin such as in the form of a treated wipe.

Method of Making Compositions

Compositions within the scope of this invention were prepared in the following manner. Mix all water soluble ingredients including preservatives, thickening polymer, optionally glycerine, and water and heat to a temperature of 70-90° C. In a separate vessel mix all oil soluble ingredients including sugar surfactant and the N-aralkylcarbonyldiamine compound(s) to a temperature of 70-90° C. Add the oil phase to the water phase at a temperature of 70-90° C. with agitation. Optionally add niacinamide at 45° C. followed by addition of fragrance and phenoxyethanol at 40° C. Cool the mixture to room temperature with mixing.

Method of Using Compositions

Composition according to the invention is intended primarily as a product for topical application to human skin, especially as an agent for conditioning and smoothening the skin, and preventing or reducing the appearance of wrinkled or aged skin, or age spots, or lightening of the skin.

More specifically, using compounds of the invention, the compositions are intended to enhance cell proliferation, enhance cell migration and/or increase epidermal thickness, all traits associated with younger, healthier skin.

In use, a small quantity of the composition, for example from 1 to 5 ml, is applied to exposed area of the skin, from a suitable container or applicator and, if necessary, it is then spread over and/or rubbed into the skin using the hand or fingers or a suitable device.

While the above summarizes the present invention, it will become apparent to those skilled in the art that modifications, variations and alterations may be made without deviating from the scope and spirit of the present invention as described and claimed herein. The invention will now be further illustrated in the following non-limiting examples.

EXAMPLES

Representative N-aralkylcarbonyldiamines of Structure I within the scope of the invention were investigated for inhibition of the muscarinic 3 receptor and the ability to induce cell proliferation in living skin equivalents.

The results below show that compounds included in this invention effectively inhibit the muscarinic 3 receptor (Table 1). Specifically, compound with $IC_{50}$ value (defined as the concentration of compound which inhibits muscarinic receptor response 50% of its maximum response) below 10 μM provide such inhibition. Further, based on testing with at least one other muscarinic 3 receptor antagonist with $IC_{50}$ value at level of 10 μM, applicants have noted that this concentration provides enhanced cell proliferation. As seen, all the novel compounds of the invention have $IC_{50}$ value well below 10 μM.

TABLE 1

| Example | Structure ID | Structure | $IC_{50}$ (μM) |
|---|---|---|---|
| 1 | 3a | 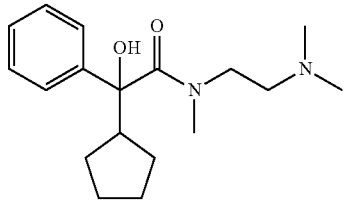 [SMILES: CN(C)CCN(C)C(=O)C(O)(c1ccccc1)C1CCCC1] | 0.44 |
| 2 | 3b | 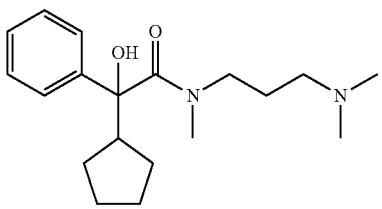 [SMILES: CN(C)CCCN(C)C(=O)C(O)(c1ccccc1)C1CCCC1] | 1.5 |
| 3 | 3c | 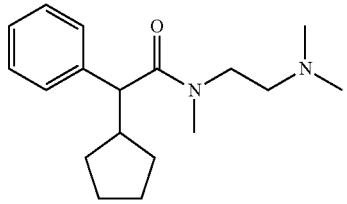 [SMILES: CN(C)CCN(C)C(=O)C(c1ccccc1)C1CCCC1] | 3.3 |
| 4 | 3d | 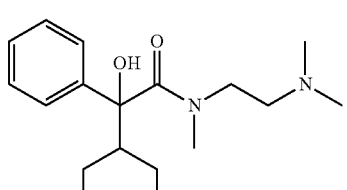 | 0.65 |

The results below show a representative N-aralkylcarbonyldiamine (3a) included in this invention effectively increasing cell proliferation in human living skin equivalents as measured by Ki-67 staining (Table 2). Specifically, this compound provides an increase in Ki-67-stained positive cells (more proliferation) of 72%.

TABLE 2

| Example | Structure ID | Structure | Concentration | % Increase in Ki-67 stained positive cells over vehicle | P-value |
|---|---|---|---|---|---|
| 5 | 3a | (structure) | 1 μM | 72 | 0.005 |

Example 6

Herein is illustrated a lotion according to the present invention with a formula as outlined in Table 3 below. This formula is packaged in a standard polypropylene bottle with screw-top. A label around the outside of the bottle specifies that the composition has effectiveness against the signs of aging including removal of fine lines and wrinkles.

TABLE 3

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Compound 3a | 0.1 |
| PHASE B | |
| Xanthan Gum | 0.20 |
| Natrosol ® 250HHR (ethyl cellulose) | 0.50 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| PHASE D | |
| Vitamin A Palmitate | 0.10 |
| Bisabolol | 0.01 |
| Vitamin A Acetate | 0.01 |
| Fragrance | 0.03 |
| Retinol 50C | 0.02 |
| Conjugated Linoleic Acid | 0.50 |

Example 7

A water-in-oil topical liquid make-up foundation according to invention is described in Table 4 below. This foundation is delivered via a glass screw-top capped bottle. The bottle is placed within an outer carton. Inside the carton is placed instructions for use including applying the foundation to the face to achieve improvements in the signs of aging including enhanced radiance.

TABLE 4

| INGREDIENT | WEIGHT % |
|---|---|
| PHASE A | |
| Cyclomethicone | 9.25 |
| Oleyl Oleate | 2.00 |
| Dimethicone Copolyol | 20.00 |
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance | 0.05 |
| PHASE G | |
| Water | Balance |
| Compound 3a | 0.1-1.0 |
| Methyl Paraben | 0.12 |
| Propylene Glycol | 8.00 |
| Niacinamide | 4.00 |
| Glycerin | 3.00 |
| Sodium Chloride | 2.00 |
| Sodium Dehydroacetate | 0.30 |

Example 8

Illustrated herein is a skin cream incorporating N-aralkylcarbonyldiamine compound(s) with our invention. The cream is deposited in a wide-mouth jar with screw-cap top.

Printed on the label of the jar are instructions that the cream will control the signs of aging such as hyperpigmentation and sagging skin.

TABLE 5

| INGREDIENT | WEIGHT % |
| --- | --- |
| Glycerin | 6.93 |
| Niacinamide | 5.00 |
| Compound 3a | 0.1 |
| Permethyl 101A[1] | 3.00 |
| Sepigel 305[2] | 2.50 |
| Q2-1403[3] | 2.00 |
| Linseed Oil | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Disodium EDTA | 0.10 |
| Glydant Plus[6] | 0.10 |
| PEG-100 Stearate | 0.10 |
| Stearic Acid | 0.10 |
| Purified Water | Balance |

[1]Isohexadecane, Presperse Inc., South Plainfield, NJ
[2]Polyacrylamide(and)C13-14 Isoparaffin(and) Laureth-7, Seppic Corporation, Fairfield, NJ
[3]dimethicone(and)dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ Example 9

Illustrative of another cosmetic personal care composition incorporating N-aralkylcarbonyldiamine compounds of our invention is the formula of Table 6. This composition is packaged in a plastic polypropylene tube with flexible side walls for pressing the composition through a tube orifice. Instructions are printed on the outside of the tube directing that the composition be applied to the face and that in a period from about 2 weeks to about 6 months, the signs of aging will have diminished.

TABLE 6

| INGREDIENT | WEIGHT % |
| --- | --- |
| Polysilicone-11 | 29 |
| Cyclomethicone | 59 |
| Petrolatum | 11 |
| Compound 3a | 0.2 |
| Dimethicone Copolyol | 0.5 |
| Sunflowerseed Oil | 0.3 |

Example 10

A skin conditioning lotion is prepared as follows:

| Ingredient | % by Weight |
| --- | --- |
| Water | Balance |
| Carbopol Ultrez 10 | 0.8 |
| Polyoxyethylene 21 stearyl ether | 0.4 |
| Polysorbate 60 | 0.3 |
| Glycerine | 10.0 |
| Preservative | 0.7 |
| Dimethicone crosspolymer | 10 |
| NaOH (50%) | 0.5 |

-continued

| Ingredient | % by Weight |
| --- | --- |
| Dimethicone | 11.0 |
| Compound 3a | 0.5 |
| Mineral oil | 2.0 |
| Polyethylene | 4 |
| Fragrance | 0.3 |

The invention claimed is:

1. An N-aralkylcarbonyldiamine compound having structure I noted below:

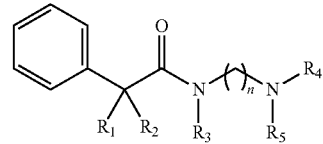

I wherein n=2, $R_1$ is hydroxyl, $R_2$ is selected from cyclohexyl or cyclopentyl, $R_3$ is selected from the group consisting of $C_1$-$C_3$ alkyl, and $R_4$ and $R_5$ are selected from the group consisting of $C_1$-$C_6$ alkyl, wherein said $C_1$ to $C_6$ alkyl group is linear, cyclic or branched and amine salts thereof.

2. A compound according to claim 1, wherein n=2, $R_1$ is hydroxyl, $R_2$ is cyclopentyl, and $R_3$, $R_4$ and $R_5$ are methyl.

3. A compound according to claim 1, wherein n=2, $R_1$ is hydroxyl, $R_2$ is cyclohexyl, and $R_3$, $R_4$ and $R_5$ are methyl.

4. A personal care composition comprising:
a) about 0.001 to 20% by wt. of composition of a compound selected from the group consisting of (i) N-aralkylcarbonyldiamine compound or compounds, (ii) mixtures of (i) where said N-aralkylcarbonyldiamine compound has Structure I noted below:

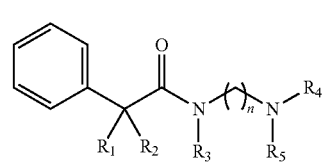

I wherein n=2, $R_1$ is hydroxyl, $R_2$ is selected from cyclohexyl or cyclopentyl, $R_3$ is selected from the group consisting of $C_1$-$C_3$ alkyl, and $R_4$ and $R_5$ are selected from the group consisting of $C_1$-$C_6$ alkyl, wherein said $C_1$-$C_6$ alkyl group is linear, cyclic or branched, and amine salts thereof; and
b) a cosmetically acceptable vehicle which may range from 5 to 99% by weight of the composition; and
c) optional skin benefit material and/or cosmetic adjunct.

5. Method of conditioning and smoothening human skin which method comprises:
a) applying compound of claim 1 to the skin of a person in need of such conditioning and smoothening;
b) measuring increase in cell proliferation by using Ki-67 assay and determining number of positive Ki-67 antibody stains relative to no treatment; and
c) correlating said increase to said conditioning and smoothening.

6. Method of conditioning and smoothening human skin which method comprises:

a) applying compound of claim 1 to the skin of a person in need of such conditioning and smoothening;
b) measuring increase in cell migration relative to no treatment; and
c) correlating said increase to said conditioning and smoothening.

7. Method of conditioning and smoothening human skin which method comprises:
a) applying compound of claim 1 to the skin of a person in need of such conditioning and smoothening;
b) measuring increase in epidermal thickness of epidermal layer relative to no treatment; and
c) correlating said increase to said conditioning and smoothening.

* * * * *